United States Patent
Bryant et al.

(10) Patent No.: US 6,562,630 B2
(45) Date of Patent: May 13, 2003

(54) METHOD FOR PREPARATION AND USE OF PRESERVATIVE-FREE IMMUNOASSAY REAGENTS

(76) Inventors: Thomas H. Bryant, Santa Fe Skies RV Park, 14 Brown Castle Ranch, Daylily #1, Santa Fe, NM (US) 87508; Nabil K. Aboukhair, 10301 C.R. 1016, Burleson, TX (US) 76028

( * ) Notice: Subject to any disclaimer, the term of this patent is extended or adjusted under 35 U.S.C. 154(b) by 0 days.

(21) Appl. No.: 09/975,784

(22) Filed: Oct. 12, 2001

(65) Prior Publication Data

US 2002/0106691 A1 Aug. 8, 2002

Related U.S. Application Data

(60) Provisional application No. 60/239,767, filed on Oct. 12, 2000.

(51) Int. Cl.$^7$ .......................... A61K 39/00; A61K 35/78
(52) U.S. Cl. .......................... 436/513; 530/379; 436/8; 436/18; 436/17; 436/513; 436/518; 435/7.1; 424/85.8; 424/88; 424/91; 424/12; 422/53
(58) Field of Search .......................... 530/379; 424/85.8, 424/88, 12, 91; 436/513, 17, 18, 8; 422/53; 435/7.1

(56) References Cited

U.S. PATENT DOCUMENTS

| | | | | | |
|---|---|---|---|---|---|
| 4,552,756 A | * | 11/1985 | Relyveld et al. | ............... | 424/88 |
| 4,716,120 A | * | 12/1987 | Tsay et al. | .................. | 436/513 |
| 5,026,545 A | * | 6/1991 | Saint-Remy et al. | ...... | 424/85.8 |
| 5,770,698 A | * | 6/1998 | Berrens | ....................... | 530/379 |

* cited by examiner

*Primary Examiner*—Long V. Le
*Assistant Examiner*—Deborah A Davis
(74) *Attorney, Agent, or Firm*—Roberts Abokhair & Mardula, LLC

(57) ABSTRACT

A method is provided for preparing preservative-free allergen test solutions in a prepared sterile environment. A sterile environment is prepared by utilizing a disinfectant wipe and a sterile barrier field. An antigen is added to a diluent to form a solution of the antigen by dispersing or suspending the antigen in the diluent. The solution is subjected to triple filtration under specific and sequential conditions to provide consistent and preservative-free allergen test solutions. Shelf life is extended by storing the solution at a temperature below 5° F. or by lyophilizing the allergen test solution.

6 Claims, No Drawings

METHOD FOR PREPARATION AND USE OF PRESERVATIVE-FREE IMMUNOASSAY REAGENTS

This application claims priority from METHOD FOR PREPARATION AND USE OF PRESERVATIVE-FREE IMMUNOASSAY REAGENTS, Serial No. 60/239,767 filed on Oct. 12, 2000, which is corporated herein in its entirety.

BACKGROUND

The purpose of this invention is to expand the number of incitants that can be utilized in allergy testing to determine which antigens or combinations of antigens are causing patient symptoms. As ozone levels and industrial pollution increase, the population at large is becoming more susceptible to adverse reactions from many sources. These include additives in food, food articles, pollens, molds, terpenes, chemicals, weeds, trees, and grasses.

Outdoor air pollution has long been thought to enhance, or at times even cause disease processes. Hippocrates mentions it in his work Air, Waters, and Places. Increased industrialization and mechanization that began around 1950 accelerated the growth of anthropogenic (manmade) pollution. According to a recent estimate, there are presently over 70,000 chemicals now in commercial production and another 700–3,000 new chemicals are being introduced every year. The U.S. Environmental Protection Agency lists 188 hazardous air pollutants either known or suspected of causing cancer, serious human health effects or ecosystem damage.

As the human immune system is taxed to detoxify from exposure to pollution, the body has become sensitized to a wider range of chemicals and natural pollutants. As a result, individuals are experiencing a wide range of both chronic and acute symptoms related to these exposures.

Presently, allergy testing commonly takes the form of intracutaneous skin tests, patch tests and blood testing such as the Radioallergosorbent Test (RAST). Skin testing comprises introducing allergens to a portion of the patients' dermis and then measuring the patients' response to the allergen. Various methods are known and used to measure the patient's response. For example, the size and color of any induced weal can be measured. U.S. Pat. No. 5,413,113 to Milne, incorporated herein by reference, describes methods of measuring galvanometric skin response to an allergen.

The skin patch is a similar method of testing for allergies and irritants. A suspected allergen or irritant is applied to normal skin under occlusion for a period of time, this application being in a controlled manner and with a suitable formulation and concentration of the test substance. Allergic eczema or irritative eczema reactions indicate a patient's sensitivity to the suspect substance. Usually the test substance is applied in a dispersion of petrolatum or aqueous solution. Means of holding the test substance in contact with the patient's dermis include the use of a foil cup or polymeric film as disclosed in U.S. Pat. No. 4,836,217 to Fischer, et al. and incorporated herein by reference.

Over 2000 substances are known as common test substances in the testing for allergens. In 1984 the American Academy of Dermatology established a list of test substances. The earlier list included: Benzocain (5% petrolatum), imidazolidinyl urea (2% aq), Thiuram mix (1% petrolatum), cinnamic alcohol (5% petrolatum) dibucaine (1% petrolatum), mercaptobenzothiazole (1% petrolatum), neomycin sulfate (20% petrolatum), p-phenylenedimine (1% petrolatum), tetracaine (1% petrolatum), p-tert.butylphenol formaldehyde resin (1% petrolatum), Thiomersal (0.1% petrolatum), formaldehyde (2% aq.), hydroxycitronellal (4% petrolatum), Carba mix (3% petrolatum), cinnamic aldehyde (2% petrolatum), rosin (colophony) (20% petrolatum), PPD mix (black rubber mix) (0.6% petrolatum), wool (lanolin) alcohols (30% petrolatum), cyclomethycaine (1% petrolatum), eugenol (4% petrolatum), Quaternium-15 (2% petrolatum), isoeugenol (4% petrolatum), mercapto mix (1% petrolatum), epoxy resin (1% petrolatum), potassium dichromate (0.5% petrolatum), caine mix less benzocaine (3% petrolatum), ethylenediamine dihydrochloride (1% petrolatum), benzoyl peroxide (1% petrolatum), balsam of Peru (25% petrolatum), Quaternium-15 (2% aq.), oak moss (abs. mousse de chene) (5% petrolatum), nickel sulfate (2.5% petrolatum). This list has subsequently been revised by the North American Contact Dermatits Group. As of 1999 this list has expanded to 50 substances with an additional 15 to be added by the year 2001. Similar lists of testing substances are available for Europe and Japan.

In skin tests, a number of apparatus have been described that introduce the allergen test substance into contact with a patient's dermis. For example, U.S. Pat. No. 3,289,670, incorporated herein by reference, discloses an apparatus that produces multiple cutaneous sites by abrading the skin and applying test substances. Intracutaneous injection of multiple test substances is disclosed in U.S. Pat. No. 4,270,548 to Brennan, incorporated herein by reference. In contrast to the test substances used in patch tests, intracutaneous allergy testing often concentrates on airborne allergies such as tree allergens, mold allergens, grass allergens, ragweed allergens, weed allergens, dust, epidermals (dander, animal hair, feathers, etc) and foods.

The intracutaneous extracts used for food testing include testing for the food groups including: whole cow's milk, whole egg, legumes, chocolate, grains (wheat, rye, barley, corn), citrus fruits (orange, grapefruit, lemon), potato family (potato, tomato, green pepper), seafood (with fish family) and cucumber (cucumber, cantaloupe, watermelon).

Intracutaneous test substances are commonly provided in either an aqueous form or in a glycerin-saline base. The aqueous form comprises a preservative in addition to the allergen and normal saline solution. For example, the 0.5% methyl paraben and 0.05% propylparaben can be added to the aqueous forms. Other aqueous preservatives include phenol and albumin. The glycerin-saline base is comprised of 50% glycerin so that additional preservative is not required. The preservative is added to increase the shelf-life of the test substance. This allows standardized test substances to be produced in a controlled environment and distributed to clinicians in an economical fashion.

However, it has been noted that some patients are sensitive to the preservatives used in the test substance preparations. The American Journal of Contact Dermatology reports of cases of allergic contact dermatitis from patient skin contact with paraben preservatives. Similarly, other patients may be allergic to glycerin, phenol or albumin. When such patients receive a series of allergy tests, they show "false positives" caused by their allergic reaction to preservative and not the named test substance.

Typical preparation of allergen extracts for intradermal use begins with a powder or ground solid form of the allergen. This powder is then dissolved or dispersed into an aqueous or normal saline solution and then filtered. Due to the nature of these powders, they often comprise the named allergen along with other foreign matter. This foreign matter is deemed to be a contaminant that lowers the specificity of the allergen extract. Patients may be allergic to the foreign matter contaminants while not being allergic to the named allergen, thus showing a "false positive."

Of the different forms of contaminants, mold, bacteria and endotoxin can be present. Special efforts must be made to insure that these forms are reduced to acceptable levels.

An additional consideration in the preparation of allergen extracts is the ability to prepare extracts of consistent biological activity. Medical clinicians rely upon this consistency in order to obtain reproducible, valid test results. Allergen extracts that are excessively active may cause allergic shock dangers to patients while extracts that are excessively inactive will not properly identify allergic responses.

As a result, there is a need for prepared allergen extracts with adequate shelf life that comprise the named test substance without added preservatives and that further have a known biological activity.

SUMMARY OF THE INVENTION

It is an object of the present invention to provide allergen testing preparations and testing protocols that are more sensitive and accurate than existing methods.

It is a further object of the present invention to provide allergen testing preparations of known shelf life and standardized biological activity that do not contain preservative agents.

It is yet another object of the present invention to provide methods of extending the shelf life of such prepared allergen testing preparations.

In accordance with one embodiment of the present invention, a method is provided for preparing preservative-free allergen test solutions in a prepared sterile environment. The method comprises preparing a sterile environment by utilizing a disinfectant wipe and a sterile barrier field. An antigen is added to a diluent to form a solution of the antigen by dispersing or suspending the antigen in the diluent. Optionally, normal saline is used as the diluent. The initial solution is maintained at a temperature selected to impede bacterial and mold growth for a period of at least 12 hours. In one embodiment, the initial solution is maintained at a temperature from 33° F. to 38° F. The initial solution is passed through a screen and first filter to become the first filtrate, wherein the screen is USP type gauze and the first filter has a pore size of 12 microns or less. The first filtrate is passed through a vacuum filter having a pore size of 2 microns. The resultant filtrate is passed through a vacuum filter having a pore size of 1.5 microns to become the second filtrate. The second filtrate is passed through a vacuum filter having a pore size of 0.22 micron. The resultant filtrate is subsequently passed through a filter having a pore size of 0.1 micron into a sterile product container. In accordance with one embodiment, the allergen test solutions are prepared to a consistent protein nitrogen concentration.

The process of the present invention allows extension of the shelf-life of the allergen test solution by storing the solution at a temperature below 5° F. Another method for extending the shelf life of the allergen of the present invention is by lyophilizing the allergen test solution.

In another embodiment, the present invention provides a method of preparing preservative-free allergen test solutions in a prepared sterile environment. The method comprises preparing a sterile environment by utilizing a disinfectant wipe and a sterile barrier field and adding an adding an antigen to a diluent solution, such as normal saline. The antigen is dispersed or dissolved in the diluent solution to form an initial supension. The initial initial solution is maintained at a temperature selected to impede bacterial and mold growth for a period of at least 12 hours. The initial solution is subjected to centrifuging for a minimum of 30 minutes, transferring a minimum of 98% by volume of the centrifuged solution to a sterile container. Diluent is added to increase the volume to 100% of the initial solution volume. The resultant solution is passed through a vacuum filter having a pore size of 0.22 micron with the resultant filtrate passed through a filter having a pore size of 0.1 micron into a sterile product container.

DESCRIPTION OF THE INVENTION

This invention relates to the method of preparing allergen testing solutions without the use of preservatives and of known biological activity, enhanced purity and known shelf-life. The invention further comprises the preferred method of extending shelf-life for these test substances.

In accordance with one embodiment of the present invention, a method is provided for preparing preservative-free allergen test solutions in a prepared sterile environment. The method comprises preparing a sterile environment by utilizing a disinfectant wipe and a sterile barrier field. An antigen is added to a diluent to form a solution of the antigen by dispersing or suspending the antigen in the diluent. Optionally, normal saline is used as the diluent. The initial solution is maintained at a temperature selected to impede bacterial and mold growth for a period of at least 12 hours. In one embodiment, the initial solution is maintained at a temperature from 33° F. to 38° F. The initial solution is passed through a screen and first filter to become the first filtrate, wherein the screen is USP type gauze and the first filter has a pore size of 12 microns or less. The first filtrate is passed through a vacuum filter having a pore size of 2 microns. The resultant filtrate is passed through a vacuum filter having a pore size of 1.5 microns to become the second filtrate. The second filtrate is passed through a vacuum filter having a pore size of 0.22 micron. The resultant filtrate is subsequently passed through a filter having a pore size of 0.1 micron into a sterile product container. In accordance with one embodiment, the allergen test solutions are prepared to a consistent protein nitrogen concentration.

The process of the present invention allows extension of the shelf-life of the allergen test solution by storing the solution at a temperature below 5° F. Another method for extending the shelf life of the allergen of the present invention is by lyophilizing the allergen test solution.

In another embodiment, the present invention provides a method of preparing preservative-free allergen test solutions in a prepared sterile environment. The method comprises preparing a sterile environment by utilizing a disinfectant wipe and a sterile barrier field and adding an adding an antigen to a diluent solution, such as normal saline. The antigen is dispersed or dissolved in the diluent solution to form an initial supension. The initial initial solution is maintained at a temperature selected to impede bacterial and mold growth for a period of at least 12 hours. The initial solution is subjected to centrifuging for a minimum of 30 minutes, transferring a minimum of 98% by volume of the centrifuged solution to a sterile container. Diluent is added to increase the volume to 100% of the initial solution volume. The resultant solution is passed through a vacuum filter having a pore size of 0.22 micron with the resultant filtrate passed through a filter having a pore size of 0.1 micron into a sterile product container.

The allergen testing solutions are presented in Table 1 and Table 2. Table 1 indicates testing solutions comprising multiple related allergens. Table 2 indicates testing solutions comprising specific allergens.

TABLE 1

ACTIVE ALLERGENS INCLUDED IN STANDARD ALLERGEN TEST SUBSTANCE MIXES

| | |
|---|---|
| MOLD MIX #1: | *Aspergillus fumigatus*, Alternaria, *hormodendrum*, *Penicillium notatum* |
| MOLD MIX #2: | Picoccum, Fusarium, Pullularia |
| MOLD MIX #3: | Fomes, *Mucor racemosus*, *Phoma herbarum* |
| MOLD MIX #4: | Cephalosporium, Botrytis, Helminthosporium, Stemphylium |
| ASPERGILLUS MIX: | Niger, *nidulans*, *glaucus*, *terreus*, *versicolor* |
| T.O.E.: MIX: | *Trichophyton mentagrophyte5*, *Trichophyton rubrum*, Epidermophyton, *Geotrichum candidum* |
| CEDAR MIX: | Redberry Juniper, Red Cedar and Mountain Cedar |
| PRIMMY GRASS MIX: | Bermuda, Johnson, Redtop, Kentucky Blue, Orchard, Timothy, Fescue, Perennial Rye |
| REGIONAL GRASS MIX: | Smooth/Hungarian Brome, Corn, Quack/Wheat, Reed Canary, Western Wheat, Crested & Cultivated Wheat |
| PRIMARY WEED MIX: | Kochia (Firebush or Burning Bush), Pigweed Mix (Spiny, Carelessweed), Dock/Sorrel Mix (Yellow, Tall, sheep Sorrell), Lamb's Quarters (Chenopodium), English Plantain, Mugwort/Sage Mix (Sagebrush, Common Mugwort, Prairie Sage, Green Sage, Dark-Leaved Mugwort), Cockleburr. |
| REGIONAL WEED MIX: | Goldenrod, Marsh Elder (Rough, Burweed, Povertyweed), Russian Thistle, WingsQale, Western Water Hemp, Greasewood |
| PRIMARY TREE MIX: | Oak Mix (Red, White, Live), Cottonwood Mix (Eastern, Western, White Poplar, Aspen), Elm Mix (American, Chinese, Fall Blooming - Cedar Elm), Birch Mix (River, Sweet, Paper, white, Yellow), Maple Mix (Sugar, Soft, Red, Box Elder), Hickory mix (Pignut, Shagbark, Shellbark, White and Pecan), Ash Mix (Green and White) |
| REGIONAL TREE MIX: | Sweet Gum, Black Walnut, Privet (Ligustrum), Mulberry, Sycamore, Mesquite, Russian Olive (has fruit). |

TABLE 2

INDIVIDUAL STANDARD ALLERGEN TEST SUBSTANCES

| | |
|---|---|
| MOLDS | Rhizopus |
| | Sparobolomyces |
| | Trichoderma |
| | Lake Algae |
| | Monilla Sito |
| | Orechyslera |
| | Curvularia Spec. |
| | Clad. Herbarum |
| | Clad. Fulvum |
| | Streptomyces |
| DUST | House Dust |
| | Mite Mix |
| DANDERS | Cat |
| | Dog |
| | Cattle |
| | Horse |
| | Feathers |
| SMUTS | Grain Smut |
| | Grass Smut |
| TERPS | Cedar |
| | Grass |
| | Pine |
| T.O.E. | Candida |
| TREES | Mountain Cedar |
| | Elm |
| | Oak |
| | Pine |
| | Mimosa |
| | Willow |
| | Mulberry |
| | Pecan |
| | Cottonwood |
| GRASSES | Johnson Grass |
| WEEDS | Ragweed |
| | Clover |
| | Dandelion |
| | Goldenrod |
| SOLUTIONS | Histamine II |
| | Serotonin II |
| | MRV |
| | Fluogen |
| IV NUTRIENTS | Magnesium Sulfate |
| | Sodium Sulfate |
| | 1% Xylocaine |
| | Sodium Bisulfite |
| NEUROTRANCMI | Methacholine |
| | Dopamine |
| | Norepinehrine |
| | Acetylcholine |
| | Epinephrine |
| CHEMICALS | Formaldehyde |
| | Orris Root |
| | Asphalt |
| | Chlorine |
| | Cigarette Smoke |
| | Cologne men's/women's |
| | Copier toner |
| | Diesel exhaust |
| | Ethanol |
| | Fireplace smoke |
| | Natural Gas |
| | Newsprint |
| | Phenol |
| | Texas Gas |
| | Toluene |
| | Isopto Carb. |
| FOODS | Avocado |
| | Beet sugar |
| | Black walnut |
| | Blueberry |
| | Buckwheat |
| | Concord grape |
| | Garbonza beans |
| | Halibut |

TABLE 2-continued

| INDIVIDUAL STANDARD ALLERGEN TEST SUBSTANCES | |
|---|---|
| | Lentil |
| | Maple sugar |
| | Rye |
| | Spelt |
| | Ultra clear |
| MISC. | House insect |
| | Stinging insect |
| | Fire ants |
| | Poison Ivy |
| | Poison Oak |
| | Cotton |

Preservative-free allergen test solutions are prepared by following the triple filtration process as described below. These solutions are tested for shelf-life by determining antigenicity of stored solutions against solutions less than 48 hours old. Three sets of prepared solutions are used for this shelf-life study. The first set is stored at a temperature of from −10 to 10° F., in substantially a solid state. The second set is stored at a temperature of from 39 to 45° F. after first being exposed to ultraviolet light sterilization.

The third set of test solutions are dehydrated by controlled temperature dehydration, utilizing a Lyopholizer apparatus. Following the waiting of various shelf-life periods, these test solutions are reconstituted with intravenous injection grade purified water and then tested for antigenicity.

As used below the term "identifying protocol" shall refer to established test methods for verification of strength and composition of the various allergens. For example, allergens that are proteinaceous in nature commonly use protein nitrogen units (PNU) and total nitrogen content as elements of the identifying protocol. Other methodology used in identifying protocols includes petri dish assay and spectrophotometric analysis.

Consistency and standardization are important to executing a quality step-by-step antigen filtration process. Using known methods of scientific research that are highly regarded among the medical community is the best method in proving the validity of a new idea. A difference of less than 10% of control parameter is the goal for each antigen. The following examples indicate methods important to the production of allergen test solutions.

EXAMPLE

Triple Filtration Process for Producing Allergen Test Solutions

Preparation

A sterile work area is prepared in a specified "antigen room" in which the Triple Filtration is performed. For example, a disinfectant wipe of Zephiran followed by the overlay with a sterile barrier field is typically adequate. The Triple Filtration is preferably performed in a specified "antigen room" designated for the sole purpose of filtration. It is imperative that temperature and humidity controls are focused to the maintenance of the dilution. The purpose of this is to minimize the evaporation of moisture and scattering of molecules from the antigen being processed and to minimize the chance of any contamination.

An initial antigen containing solution is prepared by dispersing and preferably dissolving the antigen in a suitable diluent. With many of the antigens, normal saline is suitable as the diluent. This initial solution is then held at a low temperature for a minimum of 12 hours. The temperature is selected to impede any bacterial or mold growth, yet allow dissolution or dispersion of the antigen. A typical temperature range is from 33° to 38° Farenheit.

First Filtration

The first filtration is performed in a prepared sterile work area, as explained above. The initial solution is simultaneously screened and filtered. A USP type VII gauze is used as a screen in front of an appropriate filter with a pore size of 12 microns or less. For example, Whatman filters grade 1 have a pore size of approximately 11 microns and grade 52 has a pore size approximately 7 microns. Throughout the first filtration, the room temperature is kept at below 70° F. in order to discourage mold and bacterial growth.

The initial solution is passed through this combined screen and filter, the first filtrate being collected in a sterile holding container. Should the filter become clogged, an alternate filter and screen is used to complete the first filtration.

Second Filtration

The second filtration is performed in a prepared sterile work area, as explained above. During this vacuum assisted filtration, the first filtrate is first passed through a filter with a pore size of 2.0 microns, then through a filter with a pore size of 1.5 microns. For example, the use of a Buchner vacuum filtration unit with Millipore AP20 and AP15 filter media meets this criteria. This dual pass filtration is normally performed sequentially, with the filtrate of the 2.0 micron filter media captured then fed through the 1.5 micron filter media.

Passage of the filtrate through the 1.5 micron filter is repeated if needed so that no visible residue is found on the filter. The final second filtrate may be stored for up to 72 hours at a temperature below 45° F. Throughout the second filtration, care must be taken to prevent contaminants entering from the vacuum system into the filtrate. Typically, fresh lengths of vacuum hose are connected during each filtration cycle.

Third Filtration

The third filtration is performed in a prepared sterile work area, as explained above. During this dual stage filtration, the final second filtrate is first passed through filter media with a 0.22 micron pore size, under vacuum assist. This filtrate is then further passed through a 0.1 micron pore size filter media during transfer to sterile product containers. It is essential during this third filtration step that all contaminants are excluded. The use of Falcon filter units are particularly useful in this third filtration step.

Analysis of the product allergen test solutions are performed to insure that the proper concentration of antigen in solution has been attained and that no significant bacterial or mold contamination has occurred. Analysis for antigen is typically protein nitrogen content and spectrometric analysis. Analysis for mold and bacterial contamination is performed by culturing a small sample of the product filtrate in a thioglycollate medium for 14 days at 98.6° F. (37° C.).

EXAMPLE

Centrifuge-Filtration Process for Producing Allergen Test Solutions

Preparation

A sterile work area is prepared in a specified "antigen room" in which to perform the Centrifuge-Filtration. For example, a disinfectant wipe of Zephiran followed by the overlay with a sterile barrier field is typically adequate. The Centrifuge-Filtration should be performed in a specified "antigen room" designated for the sole purpose of filtration. It is imperative that temperature and humidity controls are focused to the maintenance of the dilution. The purpose of this is to minimize the evaporation of moisture and scattering of molecules from the antigen being processed and to minimize the chance of any contamination.

An initial antigen containing solution is prepared by dispersing and preferably dissolving the antigen in a suitable diluent. With many of the antigens, normal saline is suitable as the diluent. This initial solution is then held at a low temperature for a minimum of 12 hours. The temperature is selected to impede any bacterial or mold growth, yet allow dissolution or dispersion of the antigen. A typical temperature range is from 33 to 38 degrees Farenheit.

Centrifuge

Following the low temperature period, the initial solution is centrifuged at the same temperature for a minimum of 30 minutes.

The liquid is next removed from the centrifuge and transferred to a sterile holding container for feeding into the Filtration. A minimum of 98% by volume of the liquid contents in the centrifuge is transferred. If needed, diluent is added to the holding container to bring the total volume up to that of the initial solution. Before proceeding to the first filtration, analysis of the initial solution is performed to insure that the proper concentration of antigen in solution has been attained. The centrifuge step can be repeated if necessary for a difficult antigen.

Filtration

The filtration is performed in a prepared sterile work area, as explained above. During this dual stage filtration, the liquid from the centrifuge step is first passed through filter media with a 0.22 micron pore size, under vacuum assist. This filtrate is then further passed through a 0.1 micron pore size filter media during transfer to sterile product containers. It is essential during this filtration step that all contaminants are excluded. The use of Falcon filter units are particularly useful in this filtration step.

Analysis of the product allergen test solutions are performed to insure that the proper concentration of antigen in solution has been attained and that no significant bacterial or mold contamination has occurred. Analysis for antigen is typically protein nitrogen content and spectrometric analysis. Analysis for mold and bacterial contamination is performed by culturing a small sample of the product filtrate in a thioglycollate medium for 14 days at 98.6° F. (37° C.).

After antigen test solutions have been prepared by either the Triple Filtration or Centifuge-Filtration process, it is desirable that shelf life be extended. For commercialization, it is preferred that the allergen test solutions be prepared at a centralized location. As a result, shelf-life is important.

Normal shelf-life is 14 days at a temperature of 80° F. or below. Shelf-life is extended to 45 days when the solution is maintained at a temperature of 45° F. or below. Shelf-life is further extended by freezing (cold storage) or lyophilizing (freeze-drying). Cold storage can be conveniently accomplished by placing the final product into a refrigeration unit operating at 5° F. or below. The solution will become solid as the heat of fusion is convected away from the solution container. Once in the solid (frozen) state, the antigen test solution can be stored for 18 months. When using this method of storage, the sanitary container holding the antigen product solution must be selected to allow for any expansion of the solution during freezing.

The alternate method of extending the shelf-life is lyophilization. During lyophilazation or freeze-drying, the antigen test solution is placed in a partially stoppered lyophilizer vessel in the lyophilizer unit. Lyophilization first freezes the solution, applies a vacuum to the lyophilization chamber, and heats the solution while maintaining vacuum to remove the water from the frozen state. When complete, the lyophilizer completes the stoppering of the container. It is possible to pre-freeze the solution as described above, and then transfer the frozen solutions to the lyophilizer.

Equipment needed for Antigen Solution Preparation (Triple Filtration or Centrifuge-Filtration)
1. Refrigerated Centrifuge-capable of spinning four, two hundred ml. glass containers.
2. Set of conical tube glass centrifuge containers.
3. Series of graduated pipettes for high density measurement.
4. Gravimetric Balance.
5. Spectrophotometer.
6. Tubes to test antigens on Spectrophotometer.
7. System for Nitrogen Analysis.
8. Lyophilizer-Freeze-drying system (when used).
9. Materials for current antigen-filtration process.
10. Temperature controlled shaking bath.

EXAMPLE OF TESTING FOR ANTIGENICITY

Each allergen test solution is first constituted then an appropriate shelf-life study is performed. A file for each allergen test solution should be kept including the ratio, nitrogen content, spectrograph and process of dilution. Each antigen is separately identified and its concentration is verified by the test protocol for that antigen. Both protein nitrogen and spectophotometric analysis methods are useful for this testing. Specific test protocols are reviewed by clinical professionals to insure reliable results.

Testing for antigenicity requires the selection of an experimental group of at least 100 patients, 30 to be used as a control group. A single-blinded survey is normally found to be adequate.

The Centrifuge-Filtration process described above is preferable as a means of reducing labor in preparing the allergen test solutions. However, the Centrifuge-filtration process is not to be used when antigenicity is degraded during centrifuging. For example, clinicians indicate that some allergens have volatile antigenicity character. As a result, it is important to perform antigenicity studies to determine which allergen solutions are not detrimentally affected by centrifuging.

While the present invention has been described in the context of the preferred embodiment thereof, it will be readily apparent to those skilled in the art that other modifications and variations can be made therein without departing from the spirit or scope of the present invention. For example, a graded series of allergen testing solutions where each solution contains the same allergen but in different concentrations is considered an anticipated variation to the invention. In addition, the sorting of initial antigen solutions by viscosity in order to determine which solutions can be prepared by using Centrifuge-filtration is considered a variation of this invention. Finally, the use of diatomaceous earth just prior to final filtration is considered a variation of this invention.

Accordingly, it is not intended that the present invention be limited to the specifics of the foregoing description of the preferred embodiment, but rather as being limited only by the scope of the invention as defined in the claims appended hereto.

What is claimed is:

1. A method of preparing preservative-free allergen test solutions in a prepared sterile environment comprising:

preparing a sterile environment by utilizing a disinfectant wipe and a sterile barrier field;

adding an antigen to a diluent solution;

dispersing or suspending the antigen in the diluent to form an initial solution;

maintaining the initial solution at a temperature selected to impede bacterial and mold growth for a period of at least 12 hours;

passing the initial solution through a screen and first filter to become the first filtrate, wherein the screen is gauze and the first filter has a pore size of 12 microns or less;

passing the first filtrate through a vacuum filter having a pore size of 2 microns then passing the resultant filtrate through a vacuum filter having a pore size of 1.5 microns to become the second filtrate and;

passing the second filtrate through a vacuum filter having a pore size of 0.22 micron, then passing the resultant filtrate through a filter having a pore size of 0.1 micron into a sterile product container.

2. The method of claim 1 where the allergen test solution are prepared to a consistent protein nitrogen concentration.

3. The method of claim 1 wherein the initial solution is maintained at a temperature from 33° F. to 38° F.

4. The method of claim 1 wherein shelf life of the allergen test solution is extended by storing the solution at a temperature below 5° F.

5. The method of claim 1 wherein normal saline is used as the diluent.

6. The method of claim 1 wherein shelf-life of the allergen test solution is extended by lyophilizing the allergen test solution.

* * * * *